United States Patent [19]

Katayama et al.

[11] Patent Number: 4,962,217

[45] Date of Patent: Oct. 9, 1990

[54] ORGANOSILICON COMPOUNDS HAVING A MERCAPTO GROUP IN THE MOLECULE

[75] Inventors: Seizi Katayama; Hiroshi Kanbara, both of Annaka, Japan

[73] Assignee: Shin-Etsu Chemical Co., Ltd., Japan

[21] Appl. No.: 460,788

[22] Filed: Jan. 4, 1990

[30] Foreign Application Priority Data

Jan. 13, 1989 [JP] Japan .................................. 1-6426

[51] Int. Cl.$^5$ .............................. C07F 7/08; C07F 7/18
[52] U.S. Cl. .................................................. 556/429
[58] Field of Search .......................................... 856/429

[56] References Cited

U.S. PATENT DOCUMENTS

| | | | |
|---|---|---|---|
| 3,382,196 | 5/1968 | Gowdy et al. | 556/429 X |
| 4,059,473 | 11/1977 | Okami | 556/429 X |
| 4,082,790 | 4/1978 | Speier | 556/429 |
| 4,230,816 | 10/1980 | Martin | 552/429 |
| 4,239,668 | 12/1980 | Clark et al. | 556/429 X |
| 4,415,631 | 11/1983 | Schutijser | 428/405 |
| 4,622,412 | 11/1986 | Piskoti | 556/429 |

Primary Examiner—Paul F. Shaver
Attorney, Agent, or Firm—Lowe, Price, Leblanc, Vecker & Shur

[57] ABSTRACT

Novel organosilicon compounds containing a mercapto group are provided, which compounds are of the following general formula, $HSCH_2C_6H_4(CH_2)_nSi(CH_3)_{3-m}(OR)_m$, wherein R represents a methyl group or an ethyl group, n is a value of 0,1 or 2, and m is a value or 1, 2 or 3. the ocmpounds are substantially free of any offensive odor derived from the mercapto group and are useful as a silane coupling or crosslinking agent.

9 Claims, 1 Drawing Sheet

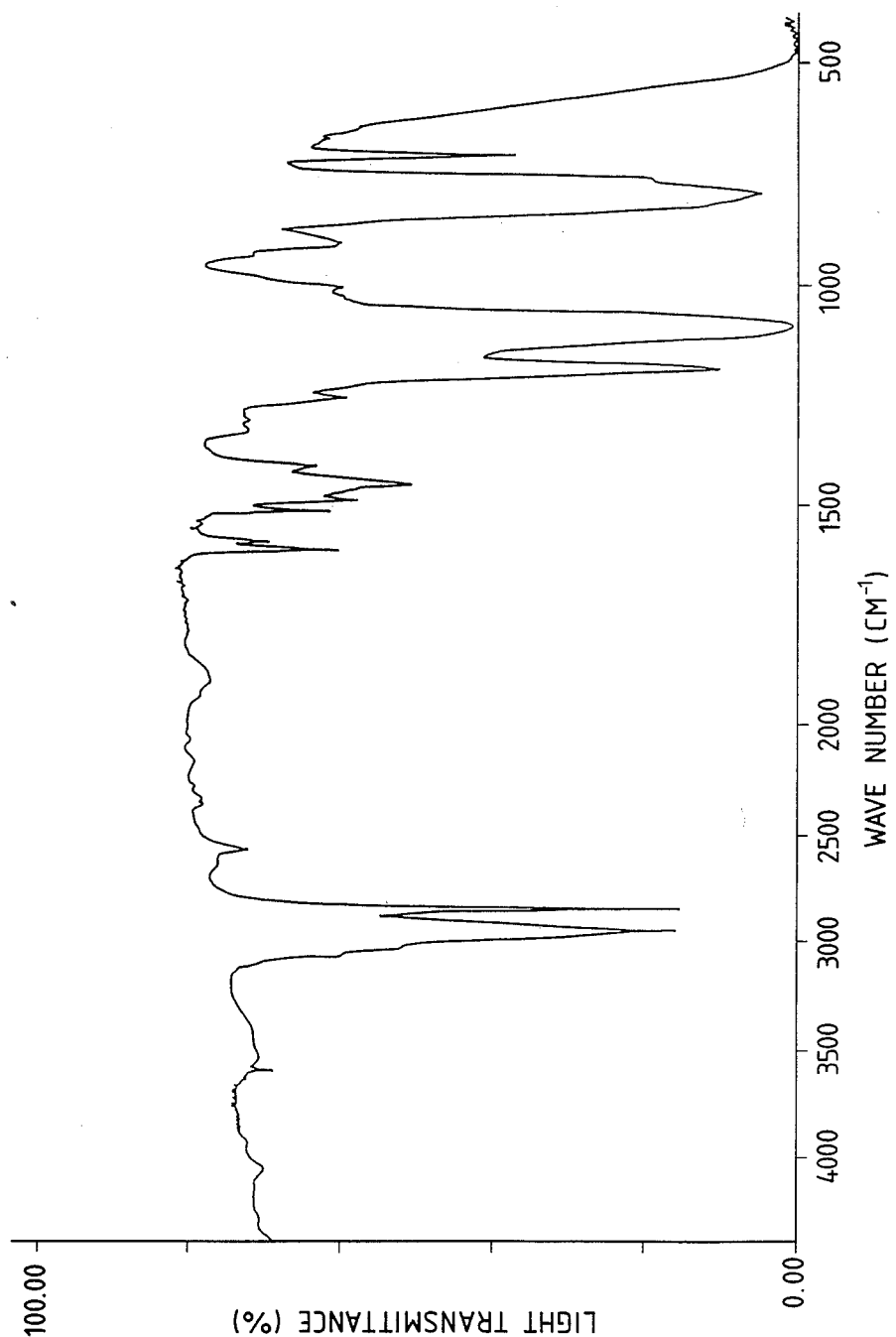

ORGANOSILICON COMPOUNDS HAVING A MERCAPTO GROUP IN THE MOLECULE

BACKGROUND OF THE INVENTION

1. Field of the Invention

This invention relates to organosilicon compounds and more particularly, to novel organosilicon compounds having a mercapto group in the molecule which are particularly useful as a silane coupling agent or crosslinking agent.

2. Description of the Prior Art

γ-Mercaptopropylalkoxysilanes and hydrolyzates thereof are known as an organosilicon compound having a mercapto group in the molecule and have been widely employed in various fields as a silane coupling agent, crosslinking agent or starting material for use in mercapto group-vinyl group reaction type UV-curable silicone compositions. See U.S. Pat. No. 4,415,631.

The mercapto group-containing silanes or low molecular weight hydrolyzates thereof usually emit a very intensive, stimulative sulfur odor derived from the mercapto group present in the molecule in view of their low boiling point and volatility. This presents a problem on working properties when such silanes are used as a coupling agent or starting material for curable compositions.

SUMMARY OF THE INVENTION

It is an object of the invention to provide a novel organosilicon compound having a mercapto group in the molecule, wherein the offensive sulfur odor is significantly reduced.

The organosilicon compound of the invention is of the following formula (1)

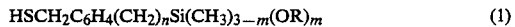

$$HSCH_2C_6H_4(CH_2)_nSi(CH_3)_{3-m}(OR)_m \quad (1)$$

wherein R represents a methyl group or an ethyl group, n is a value of 0, 1 or 2, and m is a value of 1, 2 or 3. The compound is an alkoxysilane compound having both a mercapto group and a phenylene group in the molecule.

BRIEF DESCRIPTION OF THE DRAWING

The sole FIGURE is an IR spectrum chart of a silane compound obtained in Example 1.

DETAILED DESCRIPTION OF THE INVENTION

The organosilicon compound of the invention is an alkoxysilane compound defined by the general formula (1). Specific examples of the alkoxysilane compound include those compounds of the formulae (2) to (7)

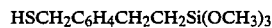
$HSCH_2C_6H_4CH_2CH_2Si(OCH_3)_3$ (2)

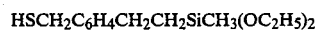
$HSCH_2C_6H_4CH_2CH_2SiCH_3(OC_2H_5)_2$ (3)

$HSCH_2C_6H_4Si(OCH_3)_3$ (4)

$HSCH_2C_6H_4SiCH_3(OCH_3)_2$ (5)

$HSCH_2C_6H_4CH_2CH_2Si(CH_3)_2(OCH_3)$ (6)

$HSCH_2C_6H_4Si(CH_3)_2(OC_2H_5)$ (7)

The organosilicon compound of the invention can be readily obtained by a known process wherein an alkoxysilane compound having a halogenated methylphenyl group corresponding to an intended product and thiourea are, for example, reacted in a polar solvent such as an alcohol, in which ammonia gas is blown.

The type of the halogen element used in the halogenated methylphenyl group-containing silane compound used as the starting material may be fluorine, chlorine, bromine or iodine. In view of the ease in availability and the reactivity, chlorine is preferred. The starting halogenated silane compound can be obtained, for example, by hydrosilylation reaction between halogenated methylstyrene and hydrogensilanes or by halogenation reaction of tolylsilanes.

The solvents used for the reaction are not critical provided that they are polar solvents capable of dissolving the starting materials. Examples of such solvents include alcohols such as methanol, ethanol, propanol, butanol, cyclohexanol and the like, ethers such as diethyl ether, dioxane, tetrahydrofuran and the like, glymes, and ketones such as acetone, methyl ethyl ketone and the like. Of these, alcohols are preferably used. More preferably, an alcohol corresponding to an alkoxy substituent of the starting alkoxysilane compound is used.

The reaction temperature is not critical and is generally in the range of from room temperature to a refluxing temperature of the solvent used.

The present invention is described by way of examples, which should not be construed as limiting the invention.

EXAMPLE 1

94 g (0.34 moles) of a chlorinated silane compound of the formula, $ClCH_2C_6H_4(CH_2)_2Si(OCH_3)_3$, 31 g (0.41 moles) of thiourea and 150 ml of methanol were placed in a 500 ml four-necked flask equipped with a gas introduction pipe, a thermometer, a reflux condenser and an agitation bar, followed by agitation in an atmosphere of nitrogen under reflux of methanol for 8 hours. After returning the reaction solution to room temperature, ammonia gas was blown into the reaction solution at a rate of 50 ml/minute for 6 hours while agitating.

Thereafter, 36 g (0.35 moles) of a 28% sodium methylate solution in methanol was added to the solution and agitated for 5 hours, followed by removal of the resultant salt by filtration, distilling off the solvent, and distillation under reduced pressure to obtain 51 g of a colorless transparent liquid with a boiling point of 127°–129° C./1 mmHg. The results of the following analyses revealed that the liquid consisted of a silane compound having a mercaptomethylphenyl group and represented by the following structural formula, $HSCH_2C_6H_4CH_2CH_2Si(OCH_3)_3$. The yield was 55%.

$^1$H-NMR spectra (CCl$_4$, tetramethylsilane external standard) δ value (ppm): 0.4–1.1(Si—C$\underline{H}_2$, 2H), 2.4–2.9-(Si—CH$_2$—C$\underline{H}_2$, 2H), 3.44(O—C$\underline{H}_3$, 9H), 3.5–3.9 (S—C$\underline{H}_2$, 2H), 6.7–7.3(C$_6\underline{H}_4$, 4H)

| | Elementary analysis (%) | | |
|---|---|---|---|
| | C | H | S |
| found: | 52.86 | 7.22 | 11.89 |
| calculated: | 52.91 | 7.40 | 11.77 |

The IR spectral chart is shown in the sole figure attached herewith.

The silane compound was subjected to an assessment test of odor by ten members at room temperature with the result that little sulfur odor was recognized by the ten members.

EXAMPLE 2

The general procedure of Example 1 was repeated except that 98 g of a chlorinated silane compound of the following formula, $ClCH_2C_6H_4CH_2CH_2SiCH_3(OC_2H_5)_2$, was used instead of the chlorinated silane compound of the formula, $ClCH_2C_6H_4CH_2CH_2Si(OCH_3)_3$ and that the methanol used as the solvent was replaced by the ethanol, thereby obtaining 55 g of a colorless, transparent liquid having a boiling point of 124° to 126° C./0.7 mmHg. This was confirmed through the following analyses to be a silane compound of the formula, $HSCH_2C_6H_4CH_2CH_2Si(CH_3)(OCH_2CH_3)_2$. The yield was 57%.

$^1$H-NMR spectra (CCl$_4$, tetramethylsilane external standard) δ value (ppm): 0.02(Si—C$\underline{H}_3$, 3H), 1.17(O—CH$_2$—C$\underline{H}_3$, 6H), 0.9–1.7 (Si—C$\underline{H}_2$, 2H), 2.4–2.8(Si—CH$_2$—C$\underline{H}_2$, 2H), 3.68(O—C$\underline{H}_2$, 4H), 3.5–3.9 (S—C$\underline{H}_2$, 2H), 6.6–7.2(C$_6$$\underline{H}_4$, 4H)

| | Elementary analysis (%) | | |
|---|---|---|---|
| | C | H | S |
| found: | 58.98 | 8.34 | 11.43 |
| calculated: | 59.11 | 8.50 | 11.27 |

This silane compound was judged as emitting little sulfur odor.

EXAMPLE 3

The general procedure of Example 1 was repeated except that 84 g of a chlorinated silane compound of the following formula, $ClCH_2C_6H_4Si(OCH_3)_3$, was used instead of the chlorinated silane compound of the formula, $ClCH_2C_6H_4CH_2CH_2Si(OCH_3)_3$, thereby obtaining 52 g of a silane compound of the formula, $HSCH_2C_6H_4Si(OCH_3)_3$ at a yield of 62%. This silane compound had a boiling point of 105° to 106° C./3 mmHg and was judged as emitting little sulfur odor.

$^1$H-NMR spectra (CCl$_4$, tetramethylsilane external standard) δ value (ppm): 3.53(O—C$\underline{H}_3$, 9H), 3.4–3.7 (S—C$\underline{H}_2$, 2H), 7.34(C$_6$$\underline{H}_4$, 4H)

| | Elementary analysis (%) | | |
|---|---|---|---|
| | C | H | S |
| found: | 49.12 | 6.58 | 13.20 |
| calculated: | 49.15 | 6.60 | 13.12 |

EXAMPLE 4

The general procedure of Example 1 was repeated except that 79 g of a chlorinated silane compound of the following formula, $ClCH_2C_6H_4Si(CH_3)(OCH_3)_2$, was used instead of the chlorinated silane compound of the formula, $ClCH_2C_6H_4CH_2CH_2Si(OCH_3)_3$, thereby obtaining 40 g of a silane compound of the formula, $HSCH_2C_6H_4Si(CH_3)(OCH_3)_2$ at a yield of 51%.

This silane compound had a boiling point of 97° to 98° C./3 mmHg and was judged as emitting little sulfur odor.

$^1$H-NMR spectra (CCl$_4$, tetramethylsilane external standard) δ value (ppm): 2.25 (Si—C$\underline{H}_3$, 3H), 3.45(O—C$\underline{H}_3$, 6H), 3.5–3.8 (S—C$\underline{H}_2$, 2H), 7.28(C$_6$$\underline{H}_4$, 4H)

| | Elementary analysis (%) | | |
|---|---|---|---|
| | C | H | S |
| found: | 52.50 | 6.98 | 14.24 |
| calculated: | 52.59 | 7.06 | 14.04 |

As will be apparent from the foregoing, the organosilicon compounds of the invention are able to provide mercapto group-containing organopolysiloxanes which are significantly reduced in the offensive odor by hydrolysis of the compounds with or without other silanes. For instance, when the compounds of the invention are used in combination with compounds with vinyl functionality such as vinyl group-containing organopolysiloxanes, there can be obtained UV-curable compositions. Since the organosilicon compounds of the invention have a phenylene group in the molecule, the UV-curable composition is able to provide a cured product which has a good heat resistance and good adhesion or wettability with respect to various substrates. The organosilicon compounds of the invention are useful as an odor-free silane coupling agent or crosslinking agent.

What is claimed is:

1. An organosilicon compound of the following general formula

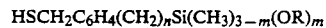

$HSCH_2C_6H_4(CH_2)_nSi(CH_3)_{3-m}(OR)_m$ wherein R represents a methyl group or an ethyl group, n is a value of 0,1 or 2, and m is a value of 1, 2 or 3.

2. An organosilicon compound according to claim 1, wherein R represents a methyl group.

3. An organosilicon compound according to claim 1, wherein R represents an ethyl group.

4. An alkoxysilane compound of the formula, $HSCH_2C_6H_4CH_2CH_2Si(OCH_3)_3$.

5. An alkoxysilane compound of the formula, $HSCH_2C_6H_4CH_2CH_2SiCH_3(OC_2H_5)_2$.

6. An alkoxysilane compound of the formula, $HSCH_2C_6H_4Si(OCH_3)_3$.

7. An alkoxysilane compound of the formula, $HSCH_2C_6H_4SiCH_3(OCH_3)_2$.

8. An alkoxysilane compound of the formula, $HSCH_2C_6H_4CH_2CH_2Si(CH_3)_2(OCH_3)$.

9. An alkoxysilane compound of the formula, $HSCH_2C_6H_4Si(CH_3)_2(OC_2H_5)$.

* * * * *